(12) United States Patent
Hardman et al.

(10) Patent No.: US 11,246,758 B2
(45) Date of Patent: *Feb. 15, 2022

(54) OPEN-CAVITY, REDUCED-PRESSURE TREATMENT DEVICES AND SYSTEMS

(71) Applicant: KCI Licensing, Inc., San Antonio, TX (US)

(72) Inventors: Ian James Hardman, Bournemouth (GB); David George Whyte, Dorset (GB); Christopher Brian Locke, Bournemouth (GB); Timothy Mark Robinson, Shillingstone (GB); James Joseph Sealy, New Milton (GB); Colin John Hall, Poole (GB); Mark Stephen James Beard, Ferndown (GB)

(73) Assignee: KCI Licensing, Inc., San Antonio, TX (US)

( * ) Notice: Subject to any disclaimer, the term of this patent is extended or adjusted under 35 U.S.C. 154(b) by 339 days.

This patent is subject to a terminal disclaimer.

(21) Appl. No.: 16/431,430

(22) Filed: Jun. 4, 2019

(65) Prior Publication Data

US 2019/0282405 A1 Sep. 19, 2019

Related U.S. Application Data

(60) Continuation of application No. 15/018,594, filed on Feb. 8, 2016, now Pat. No. 10,350,114, which is a
(Continued)

(51) Int. Cl.
*A61F 13/00* (2006.01)
*A61M 1/00* (2006.01)
(Continued)

(52) U.S. Cl.
CPC .... *A61F 13/00068* (2013.01); *A61B 17/0057* (2013.01); *A61F 13/00025* (2013.01);
(Continued)

(58) Field of Classification Search
CPC ... A61M 1/90; A61M 1/915; A61F 13/00004; A61F 13/00021; A61F 13/00025;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

US 6,216,701 B1, 04/2001, Heaton (withdrawn)
(Continued)

*Primary Examiner* — Susan S Su

(57) ABSTRACT

An open-cavity, reduced-pressure treatment device and system for treating a cavity in a patient's body, such as an abdominal cavity, is presented. In one instance, an open-cavity, reduced-pressure treatment device includes a plurality of encapsulated leg members, each having an interior portion with a leg manifold member and formed with fenestrations operable to allow fluid flow into the interior portion, and a central connection member fluidly coupled to the plurality of encapsulated leg members. The central connection member has a connection manifold member. The open-cavity, reduced-pressure treatment devices, systems, and methods allow for, among other things, removal of fluids.

14 Claims, 9 Drawing Sheets

Related U.S. Application Data continuation of application No. 13/458,006, filed on Apr. 27, 2012, now Pat. No. 9,289,327, which is a division of application No. 12/467,064, filed on May 15, 2009, now Pat. No. 8,192,409.

(60) Provisional application No. 61/109,390, filed on Oct. 29, 2008, provisional application No. 61/109,410, filed on Oct. 29, 2008, provisional application No. 61/109,448, filed on Oct. 29, 2008, provisional application No. 61/109,486, filed on Oct. 29, 2008.

(51) Int. Cl.
  *A61M 27/00* (2006.01)
  *A61B 17/00* (2006.01)

(52) U.S. Cl.
  CPC .. *A61F 13/00034* (2013.01); *A61F 13/00987* (2013.01); *A61M 1/90* (2021.05); *A61M 1/915* (2021.05); *A61M 27/00* (2013.01); *A61B 2017/00575* (2013.01); *A61B 2017/00646* (2013.01); *A61B 2017/00676* (2013.01); *A61F 13/00029* (2013.01); *A61F 13/00038* (2013.01); *A61M 1/964* (2021.05); *Y10T 29/49* (2015.01); *Y10T 29/49826* (2015.01); *Y10T 156/1052* (2015.01); *Y10T 156/1056* (2015.01); *Y10T 156/1057* (2015.01); *Y10T 156/1062* (2015.01); *Y10T 156/1304* (2015.01)

(58) Field of Classification Search
  CPC .......... A61F 13/00029; A61F 13/00034; A61F 13/00038; A61F 13/00042; A61F 13/00068; A61F 13/0203–0226; A61F 2013/00217–00234
  See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,556,101 A | 1/1971 | Economou |
| 3,568,675 A | 3/1971 | Harvey |
| 3,648,692 A | 3/1972 | Wheeler |
| 3,682,180 A | 8/1972 | McFarlane |
| 3,815,601 A | 6/1974 | Schaefer |
| 3,826,254 A | 7/1974 | Mellor |
| 3,830,238 A | 8/1974 | Kurtz et al. |
| 3,970,324 A | 7/1976 | Howat |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,250,882 A | 2/1981 | Adair |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,294,240 A | 10/1981 | Thill |
| 4,297,995 A | 11/1981 | Golub |
| 4,333,468 A | 6/1982 | Geist |
| 4,341,207 A | 7/1982 | Steer et al. |
| 4,346,711 A | 8/1982 | Agdanowski et al. |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,430,084 A | 2/1984 | Deaton |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,633,865 A | 1/1987 | Hengstberger et al. |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,728,642 A | 3/1988 | Pawelchak et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,795,435 A | 1/1989 | Steer |
| 4,815,468 A | 3/1989 | Annand |
| 4,825,866 A | 5/1989 | Pierce |
| 4,826,494 A | 5/1989 | Richmond et al. |
| 4,838,883 A | 6/1989 | Matsuura |
| 4,840,187 A | 6/1989 | Brazier |
| 4,844,072 A | 7/1989 | French et al. |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,899,965 A | 2/1990 | Usui |
| 4,906,233 A | 3/1990 | Moriuchi et al. |
| 4,906,240 A | 3/1990 | Reed et al. |
| 4,908,350 A | 3/1990 | Kramer et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,014,389 A | 5/1991 | Ogilvie et al. |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,192,266 A | 3/1993 | Wilk |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,437,683 A | 8/1995 | Neumann et al. |
| 5,441,481 A | 8/1995 | Mishra et al. |
| 5,443,848 A | 8/1995 | Kramer et al. |
| 5,466,231 A | 11/1995 | Cercone et al. |
| 5,484,399 A | 1/1996 | DiResta et al. |
| 5,484,428 A | 1/1996 | Drainville et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,637,103 A | 6/1997 | Kerwin et al. |

(56) References Cited

U.S. PATENT DOCUMENTS

| | | |
|---|---|---|
| 5,645,081 A | 7/1997 | Argenta et al. |
| 5,662,598 A | 9/1997 | Tobin |
| 5,701,917 A | 12/1997 | Khouri |
| 5,792,173 A | 8/1998 | Breen et al. |
| 5,893,368 A | 4/1999 | Sugerman |
| 5,902,260 A | 5/1999 | Gilman et al. |
| 5,938,626 A | 8/1999 | Sugerman |
| 6,042,539 A | 3/2000 | Harper et al. |
| 6,051,747 A | 4/2000 | Lindqvist et al. |
| 6,071,267 A | 6/2000 | Zamierowski |
| 6,135,116 A | 10/2000 | Vogel et al. |
| 6,174,306 B1 | 1/2001 | Fleischmann |
| 6,241,747 B1 | 6/2001 | Ruff |
| 6,264,979 B1 | 7/2001 | Svedman |
| 6,287,316 B1 | 9/2001 | Agarwal et al. |
| 6,345,623 B1 | 2/2002 | Heaton et al. |
| 6,383,162 B1 | 5/2002 | Sugarbaker |
| 6,458,109 B1 | 10/2002 | Henley et al. |
| 6,488,643 B1 | 12/2002 | Tumey et al. |
| 6,493,568 B1 | 12/2002 | Bell et al. |
| 6,537,241 B1 | 3/2003 | Odland |
| 6,553,998 B2 | 4/2003 | Heaton et al. |
| 6,626,891 B2 | 9/2003 | Ohmstede |
| 6,685,681 B2 | 2/2004 | Lockwood et al. |
| 6,695,823 B1 | 2/2004 | Lina et al. |
| 6,695,824 B2 | 2/2004 | Howard et al. |
| 6,752,794 B2 | 6/2004 | Lockwood et al. |
| 6,752,974 B2 | 6/2004 | Dunwoody et al. |
| 6,794,554 B2 | 9/2004 | Sessions et al. |
| 6,814,079 B2 | 11/2004 | Heaton et al. |
| 6,855,135 B2 | 2/2005 | Lockwood et al. |
| 6,936,037 B2 | 8/2005 | Bubb et al. |
| 6,951,553 B2 | 10/2005 | Bubb et al. |
| 6,979,324 B2 | 12/2005 | Bybordi et al. |
| 7,105,001 B2 | 9/2006 | Mandelbaum |
| 7,128,735 B2 | 10/2006 | Weston |
| 7,195,624 B2 | 3/2007 | Lockwood et al. |
| 7,276,051 B1 | 10/2007 | Henley et al. |
| 7,284,730 B2 | 10/2007 | Walsh et al. |
| 7,322,971 B2 | 1/2008 | Shehada |
| 7,338,482 B2 | 3/2008 | Lockwood et al. |
| 7,381,859 B2 | 6/2008 | Hunt et al. |
| 7,476,205 B2 | 1/2009 | Erdmann |
| 7,622,629 B2 | 11/2009 | Aali |
| 7,779,625 B2 | 8/2010 | Joshi et al. |
| 7,790,945 B1 | 9/2010 | Watson, Jr. |
| 7,846,141 B2 | 12/2010 | Weston |
| 7,951,100 B2 | 5/2011 | Hunt et al. |
| 8,062,273 B2 | 11/2011 | Weston |
| 8,114,126 B2 | 2/2012 | Heaton et al. |
| 8,216,175 B2 | 7/2012 | Hutchinson et al. |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,608,776 B2 | 12/2013 | Coward et al. |
| 8,679,081 B2 | 3/2014 | Heagle et al. |
| 8,834,451 B2 | 9/2014 | Blott et al. |
| 8,926,592 B2 | 1/2015 | Blott et al. |
| 8,936,615 B2 | 1/2015 | Pappalardo et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 9,950,100 B2 * | 4/2018 | Blott .................. A61F 13/00068 |
| 2001/0029956 A1 | 10/2001 | Argenta et al. |
| 2002/0062097 A1 | 5/2002 | Simpson |
| 2002/0065494 A1 | 5/2002 | Lockwood et al. |
| 2002/0077661 A1 | 6/2002 | Saadat |
| 2002/0115951 A1 | 8/2002 | Norstrem et al. |
| 2002/0115956 A1 | 8/2002 | Ross |
| 2002/0120185 A1 | 8/2002 | Johnson |
| 2002/0143286 A1 | 10/2002 | Tumey |
| 2002/0161317 A1 | 10/2002 | Risk et al. |
| 2003/0208149 A1 | 11/2003 | Coffey |
| 2004/0030304 A1 | 2/2004 | Hunt et al. |
| 2004/0073151 A1 | 4/2004 | Weston |
| 2004/0162512 A1 | 8/2004 | Liedtke et al. |
| 2005/0085795 A1 | 4/2005 | Lockwood et al. |
| 2005/0101922 A1 | 5/2005 | Anderson et al. |
| 2005/0131327 A1 | 6/2005 | Lockwood et al. |
| 2005/0148913 A1 | 7/2005 | Weston |
| 2005/0222544 A1 | 10/2005 | Weston |
| 2005/0261642 A1 | 11/2005 | Weston |
| 2005/0273066 A1 | 12/2005 | Wittmann |
| 2006/0029650 A1 | 2/2006 | Coffey |
| 2006/0041247 A1 | 2/2006 | Petrosenko et al. |
| 2006/0064049 A1 | 3/2006 | Marcussen |
| 2006/0079852 A1 | 4/2006 | Bubb et al. |
| 2006/0189910 A1 | 8/2006 | Johnson et al. |
| 2006/0282028 A1 | 12/2006 | Howard et al. |
| 2007/0185426 A1 | 8/2007 | Ambrosio et al. |
| 2007/0265586 A1 | 11/2007 | Joshi et al. |
| 2007/0282309 A1 | 12/2007 | Bengtson et al. |
| 2007/0293830 A1 | 12/2007 | Martin |
| 2008/0039759 A1 | 2/2008 | Holm et al. |
| 2008/0058684 A1 | 3/2008 | Ugander et al. |
| 2008/0103462 A1 | 5/2008 | Wenzel et al. |
| 2008/0103489 A1 | 5/2008 | Dahners |
| 2008/0125687 A1 | 5/2008 | Flick et al. |
| 2008/0167593 A1 | 7/2008 | Fleischmann |
| 2008/0269658 A1 | 10/2008 | Vinton et al. |
| 2009/0099519 A1 | 4/2009 | Kaplan |
| 2009/0216204 A1 | 8/2009 | Bhavaraju et al. |
| 2009/0234306 A1 | 9/2009 | Vitaris |
| 2009/0287181 A1 | 11/2009 | Kagan |
| 2010/0030132 A1 | 2/2010 | Niezgoda et al. |
| 2014/0163491 A1 | 6/2014 | Schuessler et al. |
| 2015/0080788 A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |
| CA | 2 303 085 A1 | 3/1999 |
| DE | 26 40 413 A1 | 3/1978 |
| DE | 2754775 A1 | 6/1979 |
| DE | 43 06 478 A1 | 9/1994 |
| DE | 29 504 378 U1 | 9/1995 |
| DE | 20115990 U1 | 1/2002 |
| DE | 69806842 T2 | 1/2003 |
| DE | 60118546 T2 | 8/2006 |
| DE | 102006032870 A1 | 1/2008 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 0506992 A1 | 10/1992 |
| EP | 271491 B1 | 12/1992 |
| EP | 0555293 A1 | 8/1993 |
| EP | 0620720 A1 | 10/1994 |
| EP | 0688189 A1 | 12/1995 |
| EP | 0777504 A1 | 6/1997 |
| EP | 0853950 A1 | 7/1998 |
| EP | 1018967 A1 | 7/2000 |
| EP | 1088569 A2 | 4/2001 |
| EP | 1284777 A1 | 2/2003 |
| GB | 692578 A | 6/1953 |
| GB | 2058227 A | 4/1981 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| GB | 2342584 A | 4/2000 |
| GB | 2365350 A | 2/2002 |
| JP | H 04-506760 A | 11/1992 |
| JP | 2935743 B2 | 8/1999 |

(56) References Cited

FOREIGN PATENT DOCUMENTS

| | | |
|---|---|---|
| JP | 3056429 B2 | 6/2000 |
| JP | 2002-172175 A | 6/2002 |
| JP | 2003-532504 A | 11/2003 |
| JP | 2006-503628 A | 2/2006 |
| JP | 2006-518259 A | 8/2006 |
| JP | 4129536 B2 | 8/2008 |
| JP | 2008-545456 A | 12/2008 |
| JP | 2010-508977 A | 3/2010 |
| SG | 71559 | 4/2002 |
| WO | 80/02182 A1 | 10/1980 |
| WO | 87/01027 A1 | 2/1987 |
| WO | 87/04626 A1 | 8/1987 |
| WO | 90/010424 A1 | 9/1990 |
| WO | 91/000718 A1 | 1/1991 |
| WO | 92/07519 A1 | 5/1992 |
| WO | 93/009727 A1 | 5/1993 |
| WO | 94/20041 A1 | 9/1994 |
| WO | 96/05873 A1 | 2/1996 |
| WO | 96/34636 A1 | 11/1996 |
| WO | 97/18007 A1 | 5/1997 |
| WO | 99/01173 A1 | 1/1999 |
| WO | 99/13793 A1 | 3/1999 |
| WO | 0007653 A1 | 2/2000 |
| WO | 00/42958 A1 | 7/2000 |
| WO | 00/57794 A1 | 10/2000 |
| WO | 00/59418 A1 | 10/2000 |
| WO | 0059424 A1 | 10/2000 |
| WO | 2001034223 A1 | 5/2001 |
| WO | 01/71231 A1 | 9/2001 |
| WO | 2001/89431 A1 | 11/2001 |
| WO | 0185248 A1 | 11/2001 |
| WO | 03057307 A1 | 7/2003 |
| WO | 2003/086232 A2 | 10/2003 |
| WO | 2005082435 A1 | 9/2005 |
| WO | 2006/048246 A1 | 5/2006 |
| WO | 2006056294 A1 | 6/2006 |
| WO | 2006/114637 A2 | 11/2006 |
| WO | 2006-122565 A1 | 11/2006 |
| WO | 2006116281 A2 | 11/2006 |
| WO | 2007031762 A1 | 3/2007 |
| WO | 2007/041642 A2 | 4/2007 |
| WO | 2007/109209 A2 | 9/2007 |
| WO | 2007133618 A2 | 11/2007 |
| WO | 2008014358 A2 | 1/2008 |
| WO | 2008/041926 A1 | 4/2008 |
| WO | 2008060475 A2 | 5/2008 |
| WO | 2008/064502 A1 | 6/2008 |
| WO | 2008103625 A2 | 8/2008 |
| WO | 2008040020 A3 | 12/2008 |
| WO | 2009/049058 A1 | 4/2009 |
| WO | 2009/158132 A1 | 12/2009 |
| WO | 2010/033272 A1 | 3/2010 |

OTHER PUBLICATIONS

European Search Report dated Jul. 9, 2013 for corresponding application 13157837.
Taiwanese Search Report dated Apr. 17, 2013 for corresponding TW application 098116477.
European Search Report dated Jun. 22, 2015 for corresponding application 15154703.1.
Meyer et al, "A new abdominal drain for overflowing lavage in instances of severe pancreatitis with persistent peritoneal contamination", Surg. Gynecol Obstet. Sep. 1987: 165(3): 271-273.
Poritz, "Percutaneous drainage and ileocolectomy for spontaneous intraabdominal abscess in Chrohns Disease" J. Gastrointest Surg. Feb. 2007 ; 11(2): 204-208.
Khurrum et al, "Percutaneous postoperative intra-abdominal abscess drainage after elective colorectal surgery" Tech Coloprotocl Dec. 2002: 6(3): 159-164.
Reckard et al, "Management of Intraabdominal Hypertension by Percutaneous Catheter Drainage" Journal of Vascular Interventional Journal of Vascular Interventional Radiology, vol. 16, Issue 7, pp. 1019-1021, 2005.
Latenser et al, "A Pilot Study Comparing Percutaneous Decompression with decompressive laparotomy for acute abdominal compartment syndrome in thermal injury", J Burn Care & Rehab, 23(3): 190-195, 2002.
Kubiak et al, "Reduced intra-peritoneal inflammation by negative pressure therapy moderates systemic inflammation in a porcine modiel of the abdominal compartment Syndrome (ACS)", Critical Care I, vol. 207, No. 3S, Sep. 2008, S34-35.
Kaplan, "Managing the open abdomen" Ostomy Wound Management, Jan. 2004; 50 1A supply; C2; 1-8.
Kaplan et al, "Guidelines for the Management of the Open Abdomen" Wounds Oct. 2005; 17 (Suppl 1); S1-S24.
Garner et al, "Vacuum-assisted wound closure provides early fascial reapproximation in trauma patients with open abdomens" The American Journal of Surgery, Dec. 2001; 182 (6); 630-638.
Barker et al, "Vacuum pack of technique of temporary abdominal closure; a 7-year experience with 112 patients" J Trauma Feb. 1, 2000; 48 (2): 201-206.
Brock et a;, "Temporary closure of open abdominal wounds: the vacuum pack" Am Surg Jan. 1995; 61(1): 30-35.
Sherck et al, "Covering the 'open abdomen': a better technique", Am Surg Sep. 1998; 64(9): 854-857.
Dubick et al, "Issues of concern regarding the use of hypertonic/hyperoncotic fluid resuscitation of hemorrhagic hypotension" Shock, Apr. 2006; 25(4): 321-328.
Burdette, "Systemic Inflammatory Response Syndrome", http://emedicine.medscape.com/article/168943-print, Apr. 2007.
Beamis Hyrdorphobic Rigid Canisters—http://www.bemishealthcare.com/docs/Canister Hydrophobic.pdf (date unknown).
Fink et al, "Textbook of Critical Care", 5th ed. (Philadelphia: Elsevier, 2005), 1933-1943.
International Search Report and Written Opinion dated Nov. 5, 2009; PCT International Application No. PCT/US2009/044264.
International Search Report and Written Opinion dated Nov. 18, 2009; PCT International Application No. PCT/US2009/044230.
International Search Report and Written Opinion dated Sep. 17, 2009; PCT International Application No. PCT/US2009/044240.
International Search Report and Written Opinion dated Nov. 5, 2009; PCT International Application No. PCT/US2009/044268.
International Search Report and Written Opinion dated Oct. 6, 2009; PCT International Application No. PCT/US2009/044226.
International Search Report and Written Opinion dated Oct. 15, 2009; PCT International Application No. PCT/US2009/044244.
International Search Report and Written Opinion dated Oct. 6, 2009; PCT International Application No. PCT/US2009/044266.
International Search Report and Written Opinion dated Nov. 5, 2009; PCT International Application No. PCT/US2009/044245.
International Search Report and Written Opinion dated Oct. 23, 2009; PCT International Application No. PCT/US2009/044235.
The V.A.C. TM Vacuum assisted Closure, assisting in Wound Closure, Brochure, Jan. 1996, 5 pages, 1-042, KCI®, San Antonio, Texas.
Argenta et al: "The V.A.C. TM, Case Study #4", Case Study, Mar. 1995, 1 page, 35-D-004, KCI®, San Antonio, Texas.
Argenta et al: "The V.A.C. TM, Case Study #3", Case Study, Mar. 1995, 1 page, 35-D-003, KCI®, San Antonio, Texas.
"The V.A.C.® Operations Summary, The V.A.C.® Wound Closure System Applcations", Brochure, Mar. 1997, 4 pages, 1-A-060, KCI®, San Antonio, Texas.
"The V.A.C.® Operations Summary, The V.A.C.® Wound Closure System Applcations", Brochure, Mar. 1999, 2 pages, 1-A-060, KCI®, San Antonio, Texas.
Argenta et al.: "V.A.C.® Wound Closure Device Case Study #3", Case Study, Apr. 1998, 1 page, 35-D-003, KCI®, San Antonio, Texas.
The V.A.C.® Case Study #8, Case Study, Jun. 1996, 2 pages, 35-D-008, KCI®, San Antonio, Texas.
The V.A.C.® Case Study #7, Case Study, Jun. 1996, 2 pages, 35-D-007, KCI®, San Antonio, Texas.
The V.A.C.® Case Study #6, Case Study, Jun. 1996, 2 pages, 35-D-006, KCI®, San Antonio, Texas.
The V.A.C.® Case Study #9, Case Study, Jun. 1996, 2 pages, 35-D-009, KCI®, San Antonio, Texas.

(56) References Cited

OTHER PUBLICATIONS

The V.A.C.® Case Study #5, Case Study, Aug. 1994, 1 page, 35-D-005, KCI®, San Antonio, Texas.
The V.A.C.® Case Study #4, Case Study, Aug. 1994, 1 page, 35-D-004, KCI®, San Antonio, Texas.
The V.A.C.® Case Study #3, Case Study, Aug. 1994, 1 page, 35-D-003, KCI®, San Antonio, Texas.
The V.A.C.® Case Study #2, Case Study, Aug. 1994, 1 page, 35-D-002, KCI®, San Antonio, Texas.
The V.A.C.® Case Study #1, Case Study, Aug. 1994, 1 page, 35-D-001, KCI®, San Antonio, Texas.
Smith & Nephew GmbH Nullity Action date mailed Sep. 10, 2010.
Kubiak et al, "Peritoneal Negative Pressure Therapy Prevents Multiple Organ Injury in a Chronic Porcine Sepsis and Ischemia/Reperfusion Model", Shock, vol. 34, No. 5, pp. 525-534, 2010.
EP15180495; EP Search Report; dated Dec. 15, 2015; 3 pages.
Argenta et al.: "V.A.C.® Wound Closure Device Case Study #1", Case Study, Apr. 1998, 1 page, 35-D-001, KCI®, San Antonio, Texas.
International Search Report for corresponding PCT application PCT/US2009/044264 dated May 11, 2009.
Extended European Search Report for Corresponding Application No. 191771203, dated Sep. 10, 2019.
Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

(56) References Cited

OTHER PUBLICATIONS

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
Australian Examination Report for Corresponding Application No. 2018278865, dated Aug. 23, 2019.

* cited by examiner

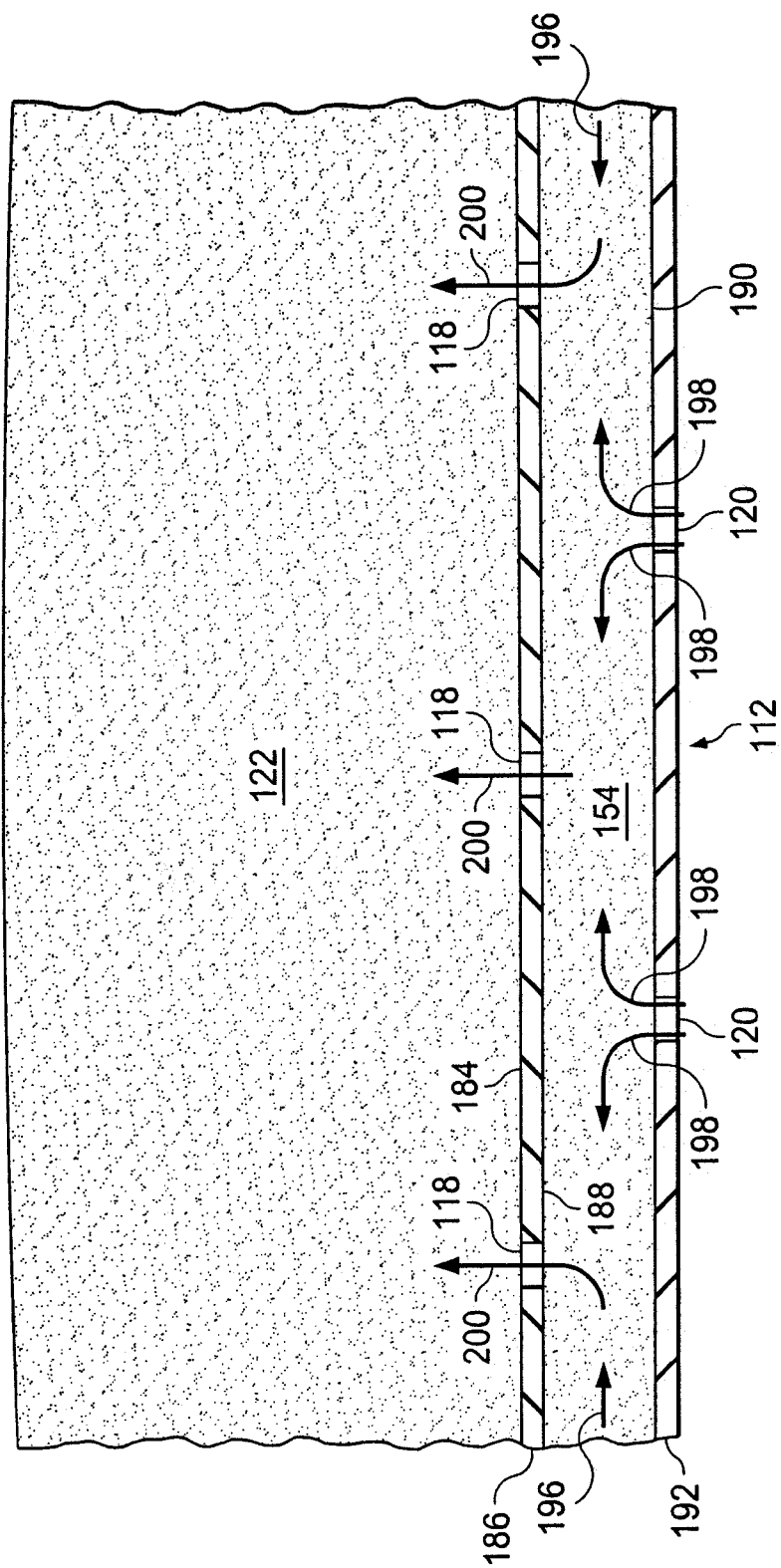

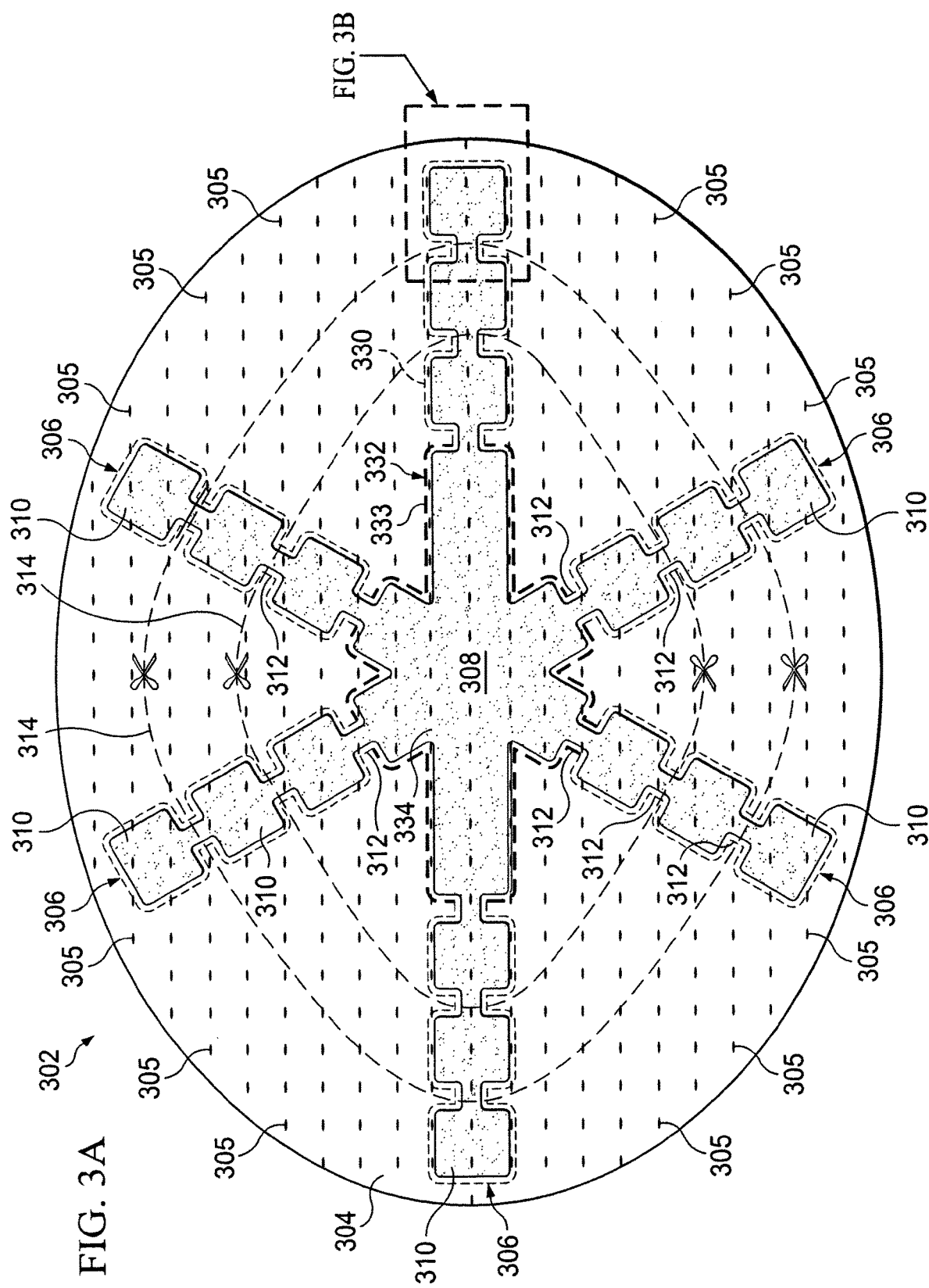

OPEN-CAVITY, REDUCED-PRESSURE TREATMENT DEVICES AND SYSTEMS

RELATED APPLICATIONS

The present application is a continuation of U.S. patent application Ser. No. 15/018,594, filed Feb. 8, 2016, entitled "Open-Cavity, Reduced-Pressure Treatment Devices and Systems," which is a continuation of U.S. patent application Ser. No. 13/458,006, now U.S. Pat. No. 9,289,327, filed Apr. 27, 2012, entitled "Open-Cavity, Reduced-Pressure Treatment Devices and Systems," which is a divisional of U.S. patent application Ser. No. 12/467,064, now U.S. Pat. No. 8,192,409, filed May 15, 2009, entitled "Open-Cavity, Reduced-Pressure Treatment Devices and Systems," which claims the benefit, under 35 USC § 119(e), of the filing of U.S. Provisional Patent Application Ser. No. 61/109,410, entitled "Reduced-Pressure, Wound-Closure System and Method," filed Oct. 29, 2008; U.S. Provisional Patent Application Ser. No. 61/109,486, entitled "Reduced-Pressure, Abdominal Treatment System and Method," filed Oct. 29, 2008; U.S. Provisional Patent Application Ser. No. 61/109,390, entitled "Open-Cavity, Reduced-Pressure Wound Dressing and System," filed Oct. 29, 2008; and U.S. Provisional Patent Application Ser. No. 61/109,448, entitled "Reduced-Pressure, Deep-Tissue Closure System and Method," filed Oct. 29, 2008. Each of the above-referenced applications are incorporated herein by reference for all purposes.

BACKGROUND

The present invention relates generally to medical treatment systems and, more particularly, to open-cavity, reduced-pressure treatment devices and systems.

Whether the etiology of a wound, or damaged area of tissue, is trauma, surgery, or another cause, proper care of the wound, or wounds, is important to the outcome. Unique challenges exist when the wound involves locations that require reentry, for example, the peritoneal cavity and more generally the abdominal cavity. Often times when surgery or trauma involves the abdominal cavity, establishing a wound management system that facilitates reentry, allows for better and easier care, and helps to address such things as peritonitis, abdominal compartment syndrome, and infections that might inhibit final healing of the wound and the internal organs. In providing such care, it may be desirable to remove unwanted fluids from the cavity, help approximate the fascia and other tissues, and finally to help provide a closing force on the wound itself at the level of the epidermis.

Currently, an abdominal opening on the epidermis may be closed using sutures, staples, clips, and other mechanical devices to allow the skin, or epidermis, to be held and pulled. Such devices cause wounds in and of themselves. Moreover, without more, if edema occurs, tremendous pressure may be placed on the closure device with potential harm resulting. For example, if pressure rises due to edema, sutures may tear out.

With respect to an overall system for allowing reentry into the abdominal cavity, a number of techniques have been developed. One approach is to place towels down into the cavity and then use clips, such as hemostats, to close the skin over the towels. While simple and fast, the results appear to have been regarded as suboptimal. Another approach is the "Bogota bag." With this approach, a bag is sutured into place to cover the open abdomen. Still another approach, sometimes called a "vac pack," has been to pack towels in the wound and then place a drain into the abdomen and cover the abdomen with a drape. Finally, a reduced pressure approach has been used. Such an approach is shown in U.S. Pat. No. 7,381,859 to Hunt et al. and assigned to KCI Licensing, Inc. of San Antonio, Tex. U.S. Pat. No. 7,381,859 is incorporated herein by reference for all purposes.

In addition to accessing the cavity for reentry, it may be desirable to remove fluids from the cavity. It may also be desirable to provide reduced-pressure therapy to the tissue or wound, including wounds that may be within the abdominal cavity. This treatment (frequently referred to in the medical community as "negative pressure wound therapy," "reduced pressure therapy," or "vacuum therapy") may provide a number of benefits, including faster healing and increased formulation of granulation tissue.

It would be desirable to provide a system and method that could remove excess fluids from an abdominal cavity, protect the interior of the abdominal cavity by providing a non-adherent barrier, and deliver reduced pressure. Further, it would be desirable to provide a system that can be readily placed in various locations in the abdominal cavity, such as paracolic gutters, is quickly installed, and that easily accommodates different size areas.

SUMMARY

Shortcomings with existing dressings and systems for open cavities, such as abdominal cavities, are addressed by the systems, apparatus, and methods of the illustrative embodiments described herein. According to one illustrative embodiment, a reduced-pressure treatment system for providing reduced-pressure treatment within a body cavity of a patient may include a treatment device having a plurality of encapsulated leg members, each encapsulated leg member having an interior portion with a leg manifold member and formed with fenestrations operable to allow fluid flow into the interior portion. The treatment device also includes a central connection member having a connection manifold member and wherein each leg manifold member is in fluid communication with the connection manifold member. The central connection member has a first side and a second, inward-facing side. The reduced-pressure treatment system further includes a manifold for disposing proximate the first side of the central connection member and operable to distribute reduced pressure to the central connection member; a sealing member for disposing on a portion of the patient's epidermis and operable to form a pneumatic seal over the body cavity; a reduced-pressure conduit; and a reduced-pressure source for producing reduced pressure. The reduced-pressure source is fluidly coupled to the reduced-pressure delivery conduit, which is fluidly coupled to a reduced-pressure interface.

According to another illustrative embodiment, an open-cavity, reduced-pressure treatment device for treating a tissue site in a body cavity includes a plurality of encapsulated leg members, each encapsulated leg member having an interior portion with a leg manifold member. The plurality of encapsulated leg members are formed with fenestrations operable to allow fluid flow into the interior portion. The open-cavity, reduced-pressure treatment device also includes a central connection member, which has a connection manifold member. The plurality of encapsulated leg members are in fluid communication with the connection manifold member.

According to another illustrative embodiment, a method of manufacturing a reduced-pressure treatment device for use in a body cavity of a patient includes the steps of:

forming a plurality of encapsulated leg members, each encapsulated leg member having an interior portion with a leg manifold member and formed with fenestrations operable to allow fluid flow into the interior portion. The method of manufacturing a reduced-pressure treatment device further includes forming a central connection member having a connection manifold member and fluidly coupling the central connection member to the plurality of encapsulated legs, wherein each leg manifold member is in fluid communication with the connection manifold member. The illustrative method may also include placing visual indicia on the non-adherent drape that indicates various sizes that might be cut.

According to another illustrative embodiment, a method of providing reduced-pressure treatment in an abdominal cavity of a patient may include the steps of: disposing a treatment device into the abdominal cavity, wherein the treatment device has a plurality of encapsulated leg members, each encapsulated leg member having an interior portion with a leg manifold member and formed with fenestrations operable to allow fluid flow into the interior portion, and a central connection member, wherein the central connection member has a connection manifold member and wherein each leg manifold member is in fluid communication with the connection manifold member. The central connection member has a first side and a second, inward-facing side. The method further includes placing at least one of the plurality of encapsulated leg members proximate a paracolic gutter in the abdominal cavity; disposing a manifold proximate the first side of the central connection member; placing a sealing member on a portion of the patient's epidermis to form a pneumatic seal over the body cavity; coupling a reduced-pressure interface to the sealing member; and coupling a reduced-pressure conduit to the reduced-pressure interface to deliver reduced pressure to the manifold. The illustrative method may further include the step of sizing the treatment device before disposing the treatment device into the body cavity.

Other objects, features, and advantages of the illustrative embodiments will become apparent with reference to the drawings and detailed description that follow.

BRIEF DESCRIPTION OF THE DRAWINGS

FIG. 1D is a schematic cross section of a portion of the system of FIG. 1A;

FIG. 3A is a schematic, plan view of another illustrative embodiment of an open-cavity, reduced-pressure treatment device;

DETAILED DESCRIPTION OF ILLUSTRATIVE EMBODIMENTS

Figure 1A:
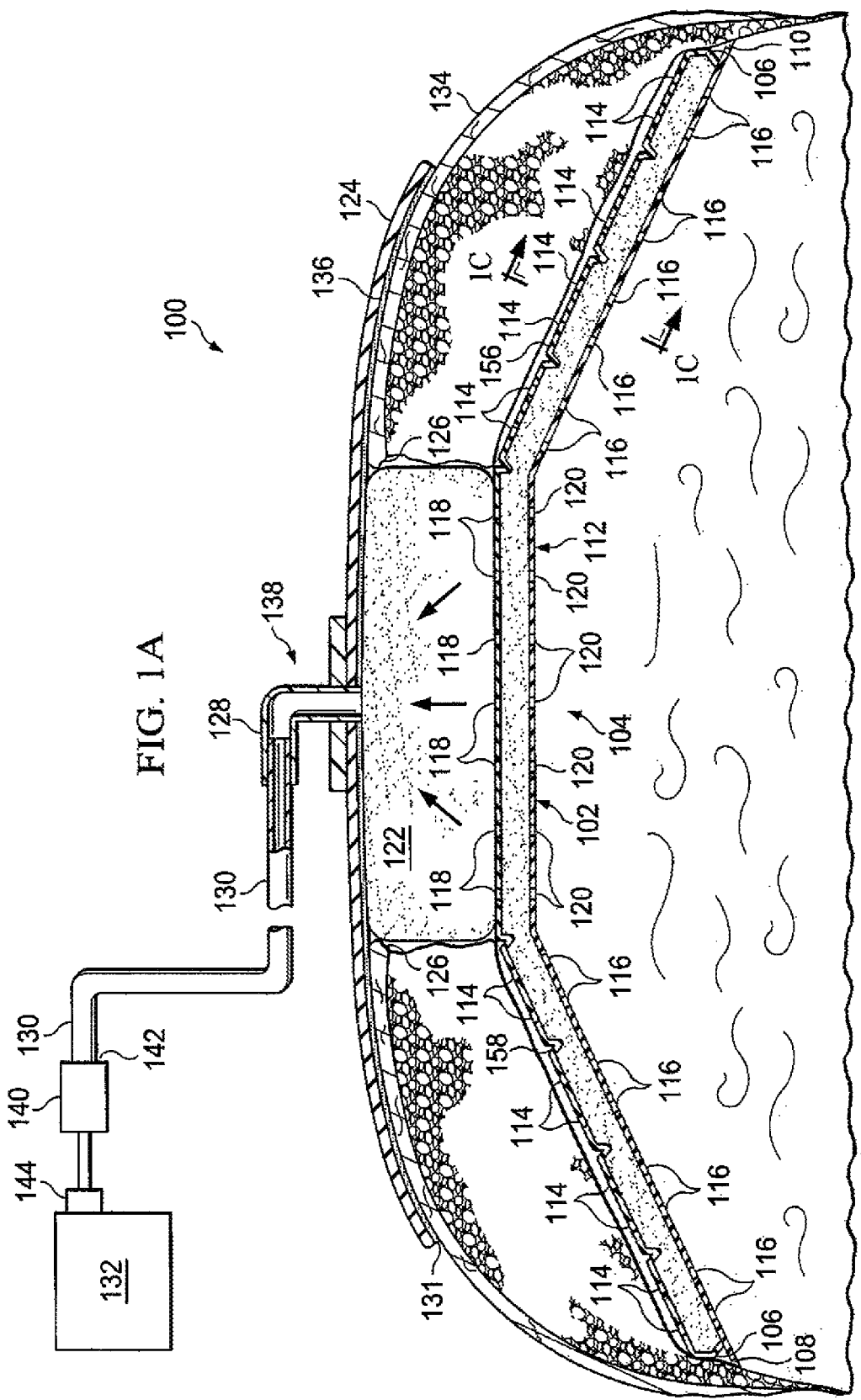
FIG. 1A is a schematic diagram, with a portion in cross section, of an illustrative embodiment of an open-cavity, reduced-pressure treatment device and system.

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Referring to FIGS. 1A-1D, an illustrative embodiment of an open-cavity, reduced-pressure system 100 and a treatment device 102 is presented. The open-cavity reduced-pressure system 100 and the treatment device 102 are for treating a tissue site 104 of a patient. The tissue site 104 may be the bodily tissue of any human, animal, or other organism, including bone tissue, adipose tissue, muscle tissue, dermal tissue, tissue, connective tissue, cartilage, tendons, ligaments, or any other tissue. In this illustrative embodiment, the tissue site 104 includes tissue in a body cavity, and in particular the abdominal cavity, and includes the abdominal contents or tissue that is proximate the abdominal cavity. Treatment of the tissue site 104 may include removal of fluids, e.g., ascites, protection of the abdominal cavity, or reduced-pressure therapy. Unless otherwise indicated, as used herein, "or" does not require mutual exclusivity.

As shown, the treatment device 102 is disposed within the abdominal cavity of the patient to treat the tissue site 104. The treatment device 102 includes a plurality of encapsulated leg members 106 that are supported by the abdominal contents, which make up a surface on which the plurality of leg members 106 are placed. One or more of the plurality of encapsulated leg members 106 may be placed in or proximate to a first paracolic gutter 108, and one or more of the plurality of encapsulated leg members 106 may be placed in or proximate to a second paracolic gutter 110. The plurality of encapsulated leg members 106 is coupled to a central connection member 112, and there is fluid communication between the plurality of encapsulated leg members 106 and the central connection member 112. The plurality of encapsulated leg members 106 and/or the central connection member 112 may be formed with fenestrations 114, 116, 118, 120 that allow fluids in the abdominal cavity to pass through. The fenestrations 114, 116, 118, 120 may take any shape, e.g., circular apertures, rectangular openings, polygons, etc., but are presented in this illustrative embodiment as slits, or linear cuts. One or more fenestrations 114, 116, 118, 120 might be omitted in alternative embodiments.

A manifold 122, or manifold pad, distributes reduced pressure to the treatment device 102. A sealing member 124 provides a pneumatic seal over body-cavity opening 126. One or more skin closure devices may be placed on a patient's epidermis 134. Reduced pressure is delivered to the manifold 122 through a reduced-pressure interface 128, which is coupled to a reduced-pressure delivery conduit 130.

A reduced-pressure source 132 delivers reduced pressure to the reduced-pressure delivery conduit 130.

The reduced pressure may be applied to the tissue site 104 to help promote removal of ascites, exudates, or other fluids from the tissue site 104. In some instances, reduced pressure may be applied to stimulate the growth of additional tissue. In some instances, only fluid removal may be desired. In the case of a wound at the tissue site 104, the growth of granulation tissue, removal of exudates, or removal of bacteria may help to promote healing of the wound. In the situation of a non-wounded or non-defective tissue, reduced pressure may be used in some instances to promote the growth of tissue that may be harvested and transplanted to another tissue site. As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Reduced pressure may initially generate fluid flow in the manifold 122, the reduced-pressure conduit 130, and proximate the tissue site 104. As the hydrostatic pressure around the tissue site 104 approaches the desired reduced pressure, the flow may subside, and the reduced pressure may be maintained. Unless otherwise indicated, values of pressure stated herein are gauge pressures.

The manifold 122 is proximate the central connection member 112. The manifold 122 may take many forms. The term "manifold" as used herein generally refers to a substance or structure that is provided to assist in applying reduced pressure to, delivering fluids to, or removing fluids from the tissue site 104. The manifold 122 typically includes a plurality of flow channels or pathways that distribute the fluids provided to and removed from the tissue site 104 around the manifold 122 and through the central connection member 112. In one illustrative embodiment, the flow channels or pathways are interconnected to improve distribution of fluids provided or removed from the tissue site 104. The manifold 122 may be a biocompatible material that is capable of being placed in contact with the tissue site 104 and distributing reduced pressure to the tissue site 104. Examples of manifold 122 may include, without limitation, devices that have structural elements arranged to form flow channels, cellular foam, such as open-cell foam, porous tissue collections, liquids, gels and foams that include or cure to include flow channels. The manifold 122 may be porous and may be made from foam, gauze, felted mat, or any other material suited to a particular biological application. In one embodiment, the manifold 122 is a porous foam and includes a plurality of interconnected cells or pores that act as flow channels. The porous foam may be a polyurethane, open-cell, reticulated foam, such as a GranuFoam® material manufactured by Kinetic Concepts, Incorporated of San Antonio, Tex. Other embodiments might include "closed cells." These closed-cell portions of the manifold may contain a plurality of cells, the majority of which are not fluidly connected to adjacent cells. The closed cells may be selectively disposed in the manifold 122 to prevent transmission of fluids through perimeter surfaces of the manifold 122. In some situations, the manifold 122 may also be used to distribute fluids such as medications, antibacterials, growth factors, and various solutions to the tissue site 104. Other layers may be included in or on the manifold 122, such as absorptive materials, wicking materials, hydrophobic materials, and hydrophilic materials.

The sealing member 124 is placed over the body-cavity opening 126 and provides a pneumatic seal adequate for the open-cavity, reduced-pressure system 100 to hold a reduced pressure at the tissue site 104. The sealing member 124 may be a cover that is used to secure the manifold 122 on the central connection member 112. The sealing member 124 may be impermeable or semi-permeable. The sealing member 124 is capable of maintaining reduced pressure at the tissue site 104 after installation of the sealing member 124 over the body-cavity opening 126. The sealing member 124 may be a flexible over-drape or film formed from a silicone-based compound, acrylic, hydrogel or hydrogel-forming material, or any other biocompatible material that includes the impermeability or permeability characteristics as desired for applying reduced pressure to the tissue site 104.

The sealing member 124 may further include an attachment means 131 to secure the sealing member 124 to the patient's epidermis 134. The attachment means 131 may take many forms; for example, an adhesive layer 136 may be positioned along a perimeter of the sealing member 124 or any portion of the sealing member 124 to provide, directly or indirectly, the pneumatic seal with the patient's epidermis 134. The adhesive layer 136 might also be pre-applied to the sealing member 124 and covered with a releasable backing, or member (not shown), that is removed at the time of application.

The reduced-pressure interface 128 may be, as one example, a port or connector 138, which permits the passage of fluid from the manifold 122 to the reduced-pressure delivery conduit 130 and vice versa. For example, fluid collected from the tissue site 104 using the manifold 122 and the treatment device 102 may enter the reduced-pressure delivery conduit 130 via the connector 138. In another embodiment, the open-cavity, reduced-pressure system 100 may omit the connector 138 and the reduced-pressure delivery conduit 130 may be inserted directly into the sealing member 124 and into the manifold 122. The reduced-pressure delivery conduit 130 may be a medical conduit or tubing or any other means for transportating a reduced pressure and fluid. The reduced-pressure delivery conduit 130 may be a multi-lumen member for readily delivering reduced pressure and removing fluids. In one embodiment, the reduced-pressure delivery conduit 130 is a two-lumen conduit with one lumen for reduced pressure and liquid transport and one lumen for communicating pressure to a pressure sensor.

Reduced pressure is generated and supplied to the reduced-pressure delivery conduit 130 by the reduced-pressure source 132. A wide range of reduced pressures may be generated or supplied by the reduced-pressure source 132. In one embodiment, the range may include the range −50 to −300 mm Hg and in another embodiment, the range may include −100 mm Hg to −200 mm Hg. In one illustrative embodiment, the reduced-pressure source 132 includes pre-set selectors for −100 mm Hg, −125 mm Hg, and −150 mm Hg. The reduced-pressure source 132 may also include a number of alarms, such as a blockage alarm, a leakage alarm, or a battery-low alarm. The reduced-pressure source 132 could be a portable source, wall source, or other unit for abdominal cavities. The reduced-pressure source 132 may selectively deliver a constant pressure, varied pressure, intermittent pressure, or continuous pressure. The fluid removed from the cavity through the reduced-pressure delivery conduit 130 could be as much as 5 L or more per day.

A number of different devices, e.g., device 140, may be added to a medial portion 142 of the reduced-pressure delivery conduit 130. For example, the device 140 might be a fluid reservoir, or canister collection member, a pressure-feedback device, a volume detection system, a blood detection system, an infection detection system, a filter, a port with a filter, a flow monitoring system, a temperature monitoring system, etc. Multiple devices 140 might be included. Some of these devices, e.g., the fluid collection member, may be formed integral to the reduced-pressure source 132. For example, a reduced-pressure port 144 on the reduced-pressure source 132 may include a filter member (not shown) that includes one or more filters and may include a hydrophobic filter that prevents liquid from entering an interior space of the reduced-pressure source 132.

Figure 2:
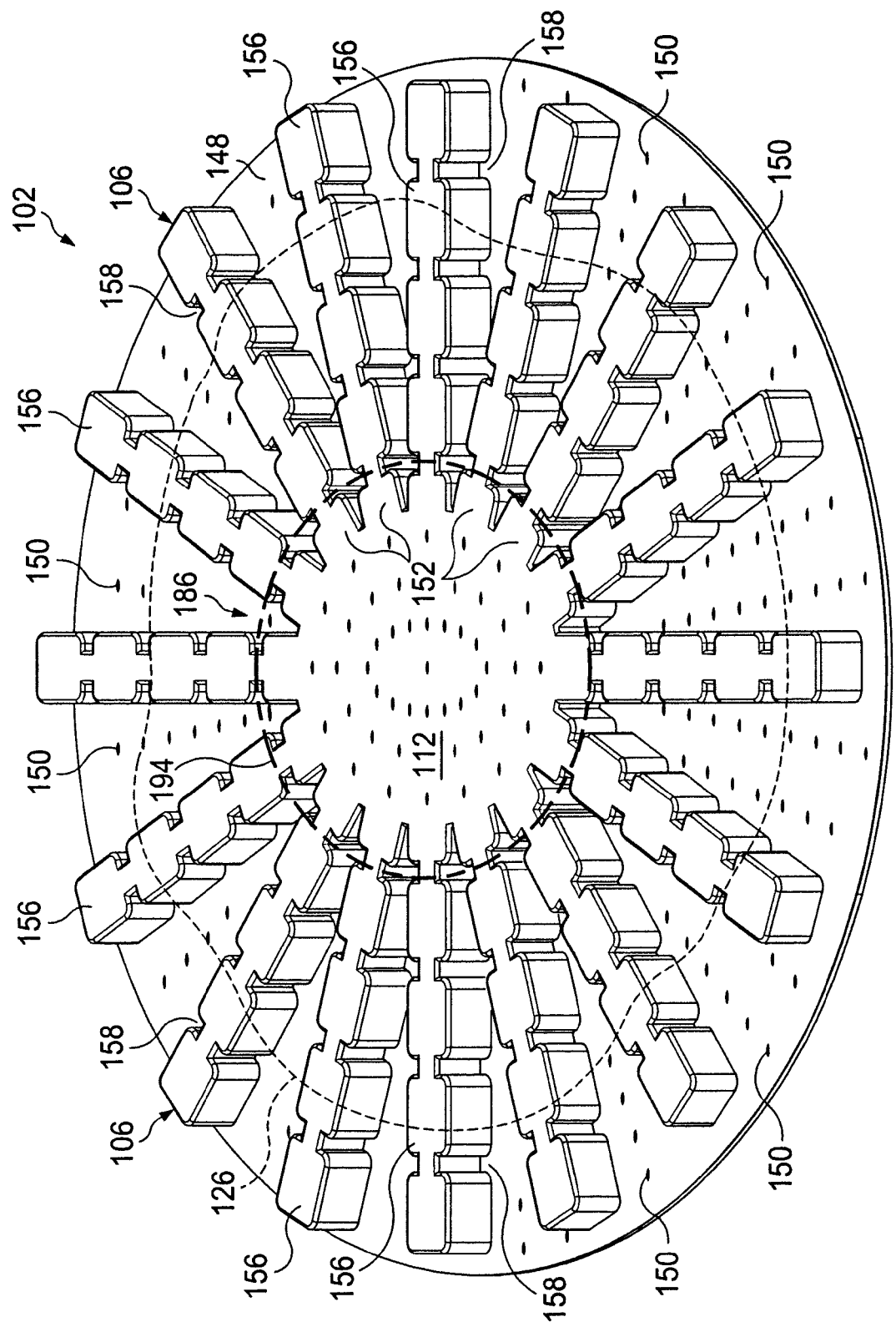
FIG. 2 is a schematic, perspective view of the illustrative embodiment of an open-cavity, reduced-pressure treatment device of FIGS. 1A-1D.

Referring now to FIGURES, 1C, 1D and 2, the treatment device 102 can include a non-adherent drape 148. The non-adherent drape 148 may be formed of a non-adherent material that inhibits tissue adhesion to the non-adherent drape 148. In one embodiment, the non-adherent drape 148 is formed from a breathable polyurethane film. The non-adherent drape 148 can include a plurality of openings, apertures, or fenestrations 150. The fenestrations can take a variety of shapes, such as circular openings, rectangular openings, polygon-shaped openings, etc., but are shown in FIG. 2 as slits, or linear cuts. Depending on the particular application of device 102, the desired fluid flow and/or pressure delivery, or other system parameters, the fenestrations can different sizes.

The treatment device 102 includes the central connection member 112 to which the plurality of encapsulated leg members 106 are coupled. The central connection member 112 includes a manifold member 154 that is encapsulated by a first connection encapsulation member 186 and a second connection encapsulation member 192. However, a portion of the central connection member can fluidly couple at leg coupling areas 152 to permit fluid communication between the central connection member 112 and the plurality of encapsulated leg members 106. The first and second connection encapsulation members may be a defined by a single piece of material or, as illustrated, more than one sheet of material.

The central connection member 112, as discussed above, can fluidly communicate with manifold 122. In one aspect, fenestrations 118, similar to the fenestrations discussed above can permit fluid communication. Additionally, or alternatively, a portion or portions of the first connection encapsulation member can be exposed to manifold 112.

Referring again to FIGS. 1A-1D, each of the plurality of encapsulated leg members 106 can include a leg manifold member 160, which may be a single manifold member that runs between the leg modules 156 and/or central connection member 112, or individual manifold components. The leg manifold member 160 is disposed within an interior portion 162 of each of the encapsulated leg members 106. Each leg manifold member 160 has a first side 164 and a second, inward-facing (patient-facing) side 166.

In one embodiment, one or more of the plurality of leg manifold members 160 can have different material properties or structures. For example, different flow rates may be desired in different encapsulated leg members 106. In one aspect, different manifold materials or manifold properties, different manifold sizes, manifold compression, the use flow restricting material structures, and/or or valves can provide different flow rates of fluid through the encapsulated leg members and/or central connection member.

In one aspect, a first leg encapsulating member 168, which can be formed with fenestrations 114, is disposed on the first side 164 of the leg manifold member 160. A second leg encapsulating member 170, which can include fenestrations 116, is disposed on the second, inward-facing side 166 of the leg manifold member 160. The second leg encapsulating member 170 may be a portion of the non-adherent drape 148. In one embodiment, the encapsulated leg members 106 can be mated with one another, for example, via drape 148. Alternatively, the leg members can be independently movable with respect to one another with the exception of their proximal end adjacent to the central connection member 112. For example, the leg members need not be connected to one another. In another embodiment, a portion of the material connecting the leg members, e.g., the non-adherent drape 148 between adjacent leg members 106, is expandable (e.g., a stretchable, flexible, deformable, and/or elastic material) and permits movement of individual leg members 106 with respect to one another.

Figure 1B:
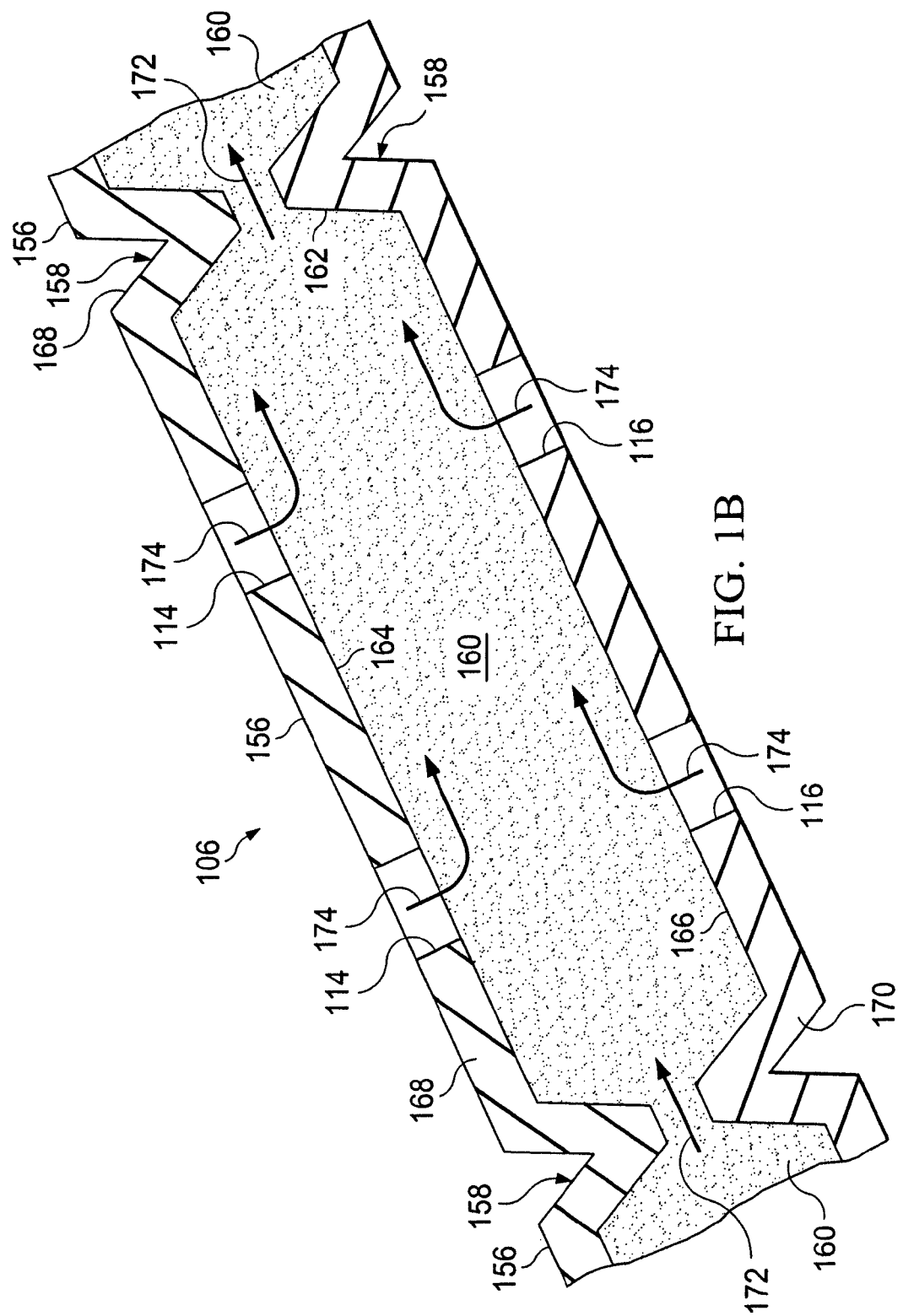
FIG. 1B is a schematic cross section of a portion of the treatment device of FIG. 1A.

As shown in the longitudinal cross section of FIG. 1B by arrows 172, fluid can flow from leg modules 156 towards the central connection member 112. As shown by arrows 174, the fluid is able to enter fenestrations 114 and 116 and flow into the leg manifold member 160 and then flow toward the central connection member 112 as represented by arrows 172.

In plan view, the encapsulated leg members 106 may take a number of different shapes, such as elongate shapes, rectangular, elliptical, etc. In one aspect, the encapsulated leg members 106 may include leg modules 156. Adjacent leg modules 156 are fluidly coupled to each other and have a manipulation zone 158 between them. In one aspect, the manipulation zone includes a weakened or perforated area to facilitate sizing of the device. For example, a clinician can cut through a leg module to size the device. By pulling on the partially cut leg module the manifold can be torn away at the next manipulation zone. In one aspect, the recessed shape of the manipulation zone 158 can inhibit accidental removal of additional leg modules. Additionally, or alternatively, the outer portion of the leg modules can be fixed to the device to inhibit unwanted manifold removal.

The encapsulated leg members 106 may also have various dimensions. If the longer dimension, e.g., lengthwise or longitudinal dimension, of the encapsulated leg 106 is $_{L1}$ and the width is $_{W1}$, then the aspect ratio is given by $_{L1}/_{W1}$. The aspect ratio may be 8.0, 7.0, 6.0, 5.0, 4.0, 3.0, 2.0 or any number in between. Moreover, other aspect ratios are possible. Generally, the width $_{W1}$ of the encapsulated leg member will be greater than a width $_{W2}$ of the central connection member 112, i.e., $_{W2}>_{W1}$. For example, in one illustrative embodiment, the encapsulated leg members 106 are approximately 270 mm long, 60 mm wide ($_{W1}$), and 10 mm thick, and the central connection member has a width parallel to the first width ($_{W1}$) of about 130 mm ($_{W2}$). Thus, in that illustrative example, the aspect ratio of the encapsulated leg 106 is approximately (270/60) or 4.5. In this same illustrative embodiment, the manipulation zones 158 have a width of about 10 mm.

Figure 1C:
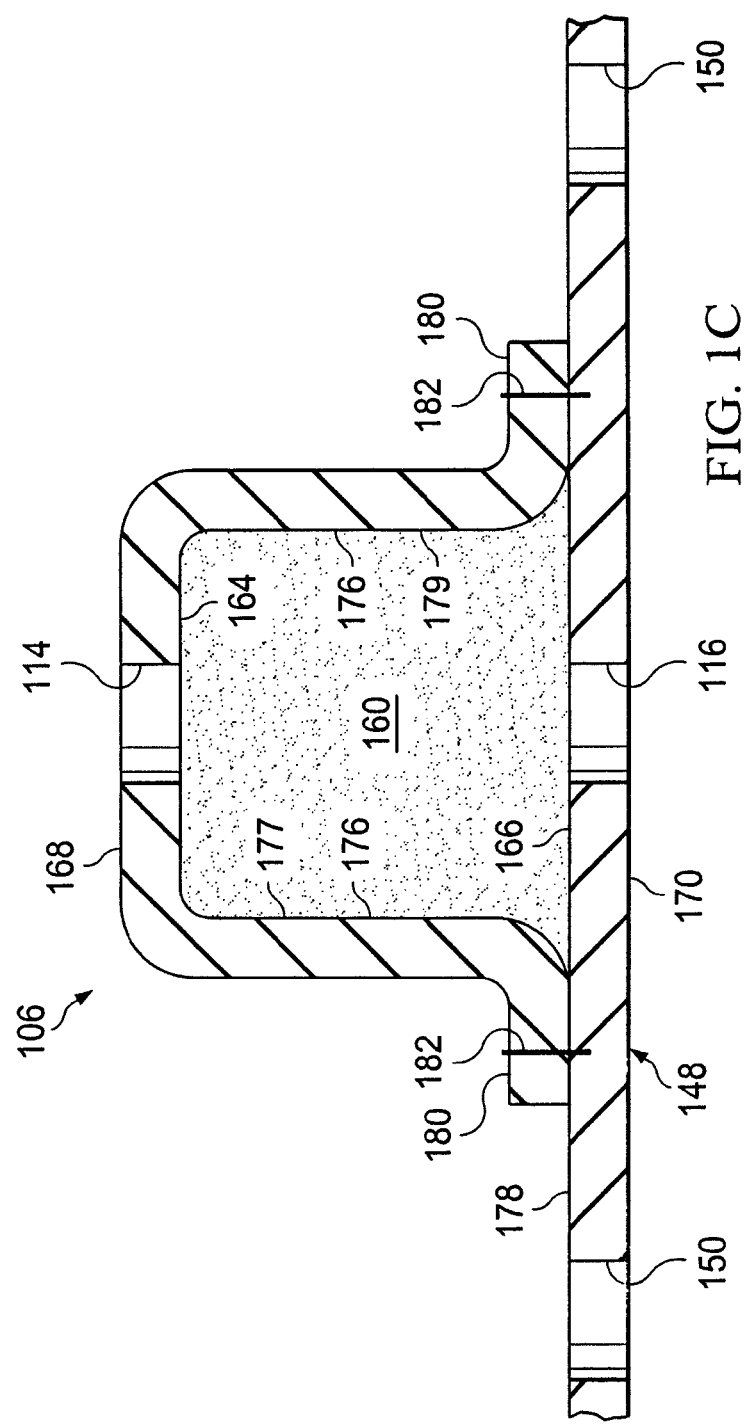
FIG. 1C is a schematic cross section of a portion of the treatment device of FIG. 1A taken along line 1C-1C.

Referring to FIG. 1C, a lateral cross section of a portion of the encapsulated leg member 106 is presented. As before, it can be seen that the first side 164 of the leg manifold member 160 is covered with the first leg encapsulating member 168, and that the second, inward-facing side 166 of the leg manifold member 160 is covered by the second leg encapsulating member 170, which in this instance is a portion of the non-adherent drape 148. Thus, in this illustrative embodiment, the fenestrations 116 may be some of the plurality of fenestrations 150 in the non-adherent drape 148. In this illustrative embodiment, a peripheral edges 176 of the leg manifold member 160 are also covered by a portion of the first leg encapsulating member 168. The peripheral edges 176 include a first lateral edge 177 and a second lateral edge 179. The first leg encapsulating member 168 covers the first side 164 and the peripheral edges 176 and extends onto a first surface 178 of the non-adherent drape 148 and forms extensions 180. The extensions 180 have been coupled to the second leg encapsulating member 170 by welds 182. The first leg encapsulating member 168 may, however, be coupled to the second leg encapsulating member 170 using any known technique, including welding (e.g., ultrasonic or RF welding), bonding, adhesives, cements, etc.

Referring again to FIG. 1D and FIG. 2, the central connection member 112 includes the connection manifold member 154 that is encapsulated within the first connection encapsulation member 186, which has fenestrations 118. The first connection encapsulation member 186 is disposed on a first side 188 of the connection manifold member 154. The second connection encapsulation member 192 is disposed on a second, inward-facing side 190 of the connection manifold member 154. The second connection encapsulation member 192 is formed with fenestrations 120. The first connection encapsulation member 186 has a peripheral zone or edge 194 as shown in FIG. 2. In a similar fashion, the second connection encapsulation member 192 has a peripheral zone or edge (not explicitly shown) that lines up with the peripheral edge 194. The peripheral edge 194 of the first connection encapsulation member 186 is coupled to peripheral edge of the second connection encapsulation member 192, except at the leg coupling areas 152 in order to allow fluid within the plurality of encapsulated leg members 106 to flow into the connection manifold member 154 as suggested by arrows 196 in FIG. 1D. Fluid may also enter directly into the connection manifold member 154 by flowing through fenestrations 120 as suggested by arrows 198. The manifold 122 is disposed proximate to the first connection encapsulation member 186, and when a reduced pressure is applied to the manifold 122, the reduced pressure causes fluid to flow from the connection manifold member 154 through fenestrations 118 and into the manifold 122 as suggested by arrows 200. The fluid continues to flow in the direction of the reduced-pressure interface 128 through which the fluid is removed to the reduced-pressure delivery conduit 130.

Referring to FIGS. 1A-1D and 2, in operation, the illustrative open-cavity, reduced-pressure system 100 may be used by first sizing the treatment device 102 as will be explained further below in connection with FIG. 3A. The non-adherent drape 148 with the plurality of encapsulated leg members 106 is disposed within the abdominal cavity through the body-cavity opening 126 and is distributed against the abdominal contents; this may include placing at least one encapsulated leg member 106 in or proximate the first paracolic gutter 108, the second paracolic gutter 110, or behind the liver, etc. Once the treatment device 102 has been distributed, the manifold 122 is placed adjacent a first side 184 of the first connection encapsulation member 186. The sealing member 124 may then be applied over the body-cavity opening 126 to provide a pneumatic seal over the body-cavity opening 126.

In addition to the sealing member 124, the body-cavity opening 126 may be further closed or reinforced using mechanical closing means, e.g., staples, or using a reduced-pressure closure system. The sealing member 124 may be applied in a number of ways, but according to one illustrative embodiment, the releasable backing member that is on the adhesive layer 136 of the sealing member 124 is removed and then the sealing member 124 is placed against the patient's epidermis 134 about the body-cavity opening 126. The reduced-pressure interface 128, such as port 138, is then attached to the sealing member 124 such that reduced pressure can be delivered by the interface 128, through the sealing member 124, and to the manifold 122. The reduced-pressure delivery conduit 130 is fluidly coupled to the reduced-pressure interface 128 and to the reduced-pressure port 144 on the reduced-pressure source 132.

The reduced-pressure source 132 is activated and thereby provides reduced pressure into the reduced-pressure delivery conduit 130, which delivers the reduced pressure to the reduced-pressure interface 128 and into the manifold 122. The manifold 122 distributes the reduced pressure and draws fluid through fenestrations 118 from the connection manifold member 154. The connection manifold member 154 draws fluid from the abdominal cavity through fenestrations 120 and pulls fluid from the plurality of encapsulated leg members 106 as suggested by arrows 196. Fluid from the abdominal cavity flows into the plurality of encapsulated leg members 106 through fenestrations 114 on the first leg encapsulating member 168 and through fenestrations 116 on the second leg encapsulating member 170 and then flows through the leg as suggested by arrows 172 towards the connection manifold member 154. The fluid then flows through the manifold 122, the reduced-pressure interface 128, and into the reduced-pressure delivery conduit 130.

Figure 3B:
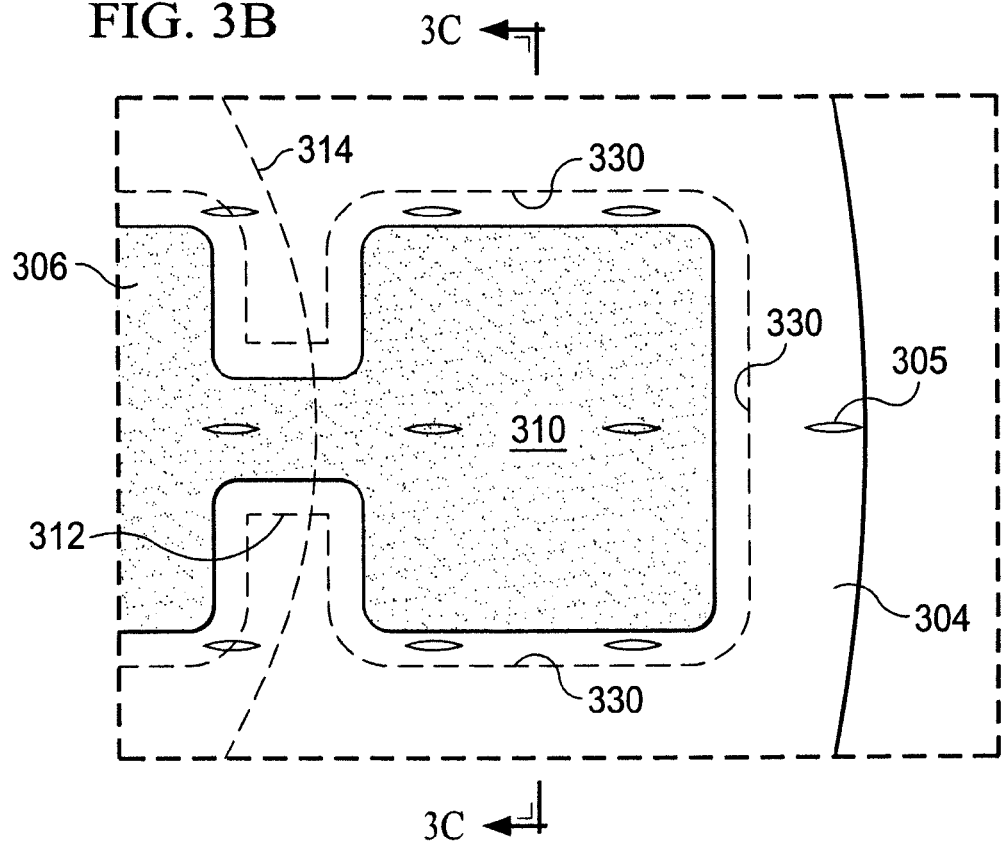
FIG. 3B is a schematic, plan view of a portion of the treatment device of FIG. 3A.
Figure 3C:
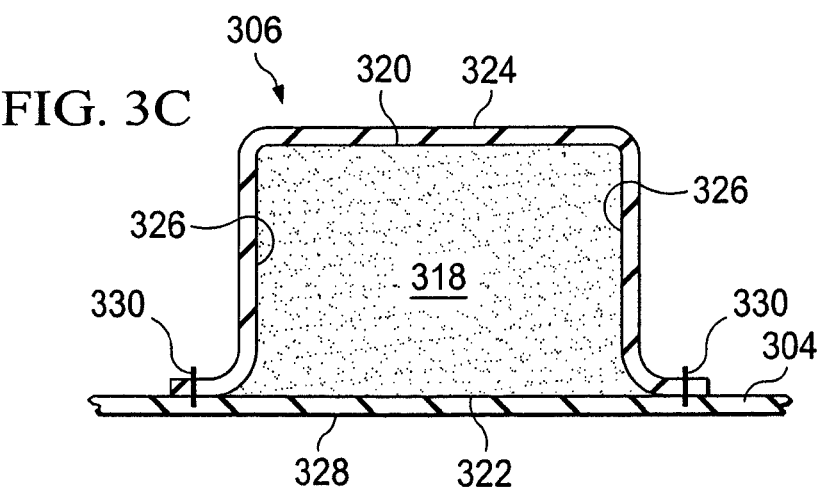
FIG. 3C is a schematic cross section of a portion of the treatment device of FIG. 3B taken along line 3C-3C.

Referring now to FIGS. 3A-3C, another illustrative embodiment of an open-cavity, reduced-pressure treatment device 302 is presented. The open-cavity, reduced-pressure treatment device 302 is analogous in most respects to the treatment device 102 of FIGS. 1A-1D. The open-cavity, reduced-pressure treatment device 302 has a non-adherent drape 304, a plurality of encapsulated leg members 306, and a central connection member 308. In this particular illustrative embodiment, the non-adherent drape 304 is formed generally with an oval or arcuate shape. The non-adherent drape 304 is formed with a plurality of fenestrations 305. The non-adherent drape 304 forms the second leg encapsulating member (see by analogy second leg encapsulating member 170 in FIG. 1B) and the second connection encapsulation member (see by analogy 192 in FIG. 1D). As such, the plurality of fenestrations 305 serves as flow channels for the plurality of encapsulated leg members 306 and the central connection member 308 on the second, inward-facing side. The non-adherent drape 304 could also be used on the first side of the plurality of encapsulated leg members 306 and the central connection member 308.

Each of the encapsulated leg members 306 may be formed with a plurality of leg modules 310 with manipulation zones 312 between the plurality of leg modules 310. As with the manipulation zone 158 in FIGS. 1A-D, the manipulation zones 312 facilitate movement of the plurality of encapsulated leg members 306 within the body cavity and provide an easier location at which to cut the plurality of encapsulated leg members 306 when the open-cavity, reduced-pressure treatment device 302 is being sized for a particular application. In this regard, visual indicia 314 may be added on the non-adherent drape 304 to help the healthcare provider know where to cut the non-adherent drape 304 for different sizes of application within the cavity. The visual indicia 314 may comprise cut lines, or graduations, that preferably run through the manipulation zones 312. The manipulation zones 312 provide a convenient and easy location for cutting the open-cavity, reduced-pressure treatment device 302.

Referring to FIG. 3C, a lateral cross section of a portion of an encapsulated leg member 306 is presented. The plurality of encapsulated leg members 306 are formed with a leg manifold member 318 having a first side 320 and a second, inward-facing (patient-facing) side 322. A first leg encapsulating member 324 covers the first side 320 of the leg manifold member 318 and covers a lateral zone or edge 326 of the leg manifold member 318. The second, inward-facing side 322 of the leg manifold member 318 is covered by a second leg encapsulating member 328, which in this embodiment is a portion of the non-adherent drape 304. The first leg encapsulating member 324 is coupled to the second leg encapsulating member 328 by any means known in the art, such as by welding (e.g., ultrasonic or RF), bonding, adhesives, cements, etc. In this illustrative embodiment, the first leg encapsulating member 324 and the second leg encapsulating member 328 are coupled by a weld 330. Referring to FIG. 3B, the weld 330 is shown along the perimeter of the plurality of leg modules 310.

Referring again to FIG. 3A, the central connection member 308 is formed analogously to the central connection member 112 in FIG. 2. A first connection encapsulation member 334 and a second connection encapsulation member of the central connection member 308 are coupled along a peripheral edge 332 using a weld 333 or another coupling technique, such as those previously mentioned. The peripheral edge 332 is not sealed, however, proximate each of the encapsulated leg members 306 in order to provide a channel for fluid to flow from the plurality of encapsulated leg members 306 into the central connection member 308.

According to one illustrative approach to constructing the open-cavity, reduced-pressure treatment device 302, the non-adherent drape 304, which is already formed with the plurality of fenestrations 305 and that has visual indicia 314 is provided. The leg manifold member 318 is disposed adjacent the non-adherent drape 304. The central connection manifold 308 is disposed adjacent to the leg manifold member 318 or may be formed integral with leg manifold member 318. The first connection encapsulation member 334 is placed on the central connection member 308, and the first leg encapsulating member 324 is placed over the leg manifold member 318. The first connection encapsulation member 334 and the first leg encapsulating member 324 may be formed from an integral sheet. Next, the welds 330 and 333 are applied.

In an alternative embodiment for manufacturing an open-cavity, reduced-pressure treatment device, a first non-adherent drape 304, which includes fenestrations, may be provided and the leg manifold member 318 and the central connection manifold 308 disposed on the first non-adherent drape 304. A second non-adherent drape, which has fenestrations, is placed over the first non-adherent drape 304, the leg manifold member 318, and the central connection manifold 308. Next, a plurality of welds (e.g., thermal or RF or another coupling techniques used) are made, such as with the welds 330. The first non-adherent drape 304 and the second non-adherent drape may be cut to size before or after assembly. By using two drapes, the first non-adherent drape 304 and the second non-adherent drape may provide better distribution of reduced pressure and may ease the manufacturing process.

The fenestrations may be formed before or after assembly. The perimeter of the first non-adherent drape 304 and the second non-adherent drape may be welded. Other points may be welded between the drapes to form a single unit. In another alternative embodiment, the drapes may initially be placed and welded without fenestrations, and then fenestrations added to the drapes so that the fenestrations align. The fenestrations might also be formed using an electrical member that cuts and seals at the same time to form aligned, "button hole" fenestrations through the two drapes.

Figure 4:
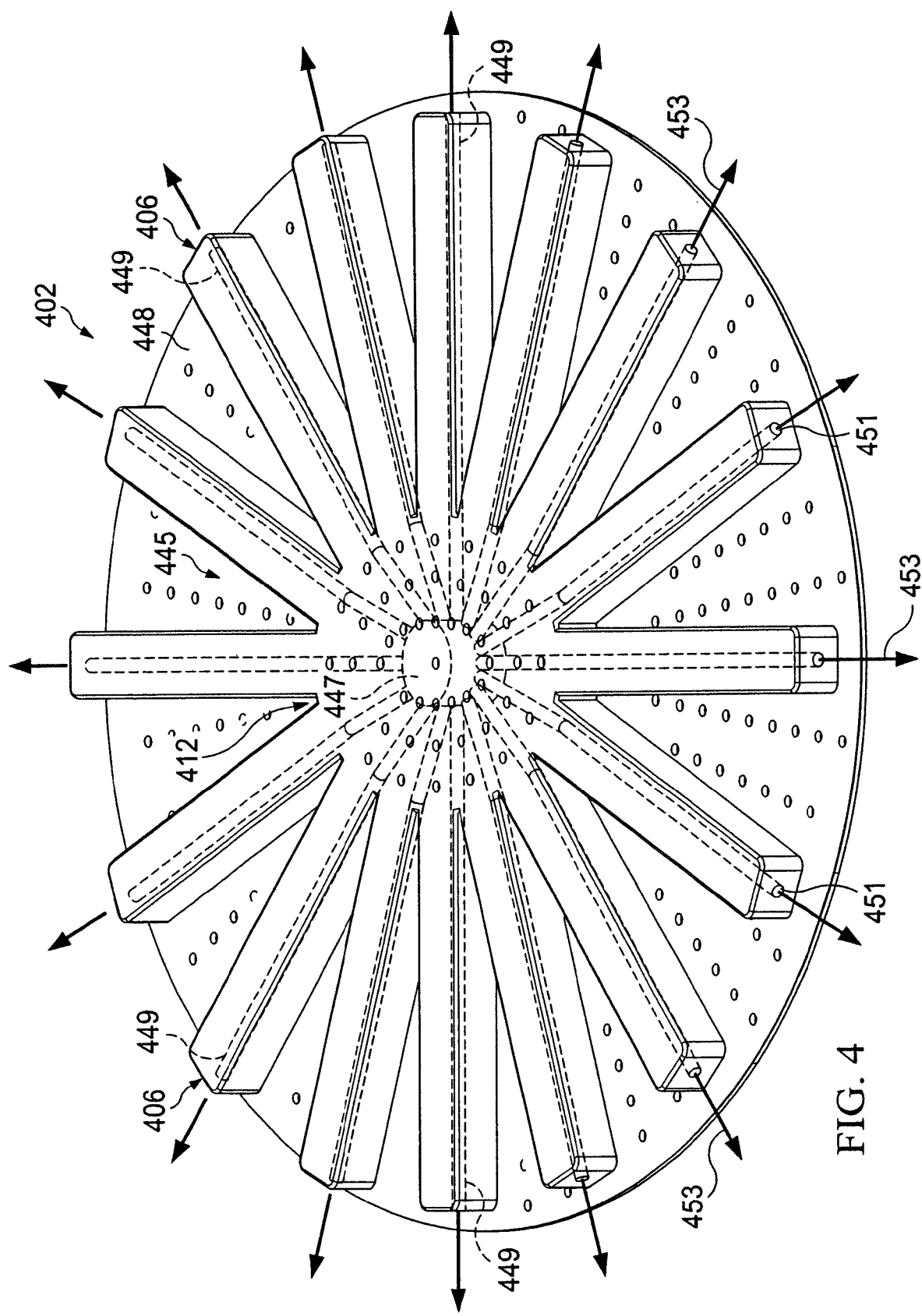
FIG. 4 is schematic, perspective view of another illustrative embodiment of an open-cavity, reduced-pressure treatment device.

Referring now to FIG. 4, another illustrative embodiment of an open-cavity, reduced-pressure treatment device 402 is presented. The open-cavity, reduced-pressure treatment device 402 is similar to the treatment device 102 shown in FIG. 2, and to indicate analogous parts, reference numerals have been indexed by 300. The open-cavity, reduced-pressure treatment device 402 differs primarily in that a fluid delivery subsystem 445 is included. A plurality of encapsulated leg members 406 are shown without leg modules, and the fenestrations are shown with a circular shape. As noted before, the plurality of encapsulated leg members 406 may be formed with or without leg modules. The fluid delivery subsystem 445 allows various fluids, such as medicines or irrigation fluids, to be delivered into the cavity. The delivered fluids may then be removed by the open-cavity, reduced-pressure treatment device 402. The fluid delivery subsystem 445 includes a central port 447, which may be placed on or in a central connection member 412, for connecting to a conduit (not shown) that delivers the fluid from a location external to the central port 447. Fluidly coupled to the central port 447 is a plurality of fluid-delivery conduits 449. The plurality of fluid-delivery conduits 449 may be located anywhere on a non-adherent drape 448, but in this illustrative embodiment, are disposed in the plurality of encapsulated leg members 406. The plurality of fluid-delivery conduits 449 are opened on their distal ends 451 to allow the delivery of fluid therethrough. The flow of fluid through the distal ends 451 of the plurality of fluid-delivery conduits 449 is suggested by arrows 453.

In use, the open-cavity, reduced-pressure treatment device 402 may be used in a fashion analogous to that of the treatment devices 102 and 302, but at various times or even continuously, it may be desirable to deliver a fluid through the fluid delivery subsystem 445. For example, it may be desirable to flush the abdominal cavity with an irrigation fluid or to deliver periodic doses of medicine.

Another illustrative embodiment for using an open-cavity, reduced-pressure treatment device (e.g., cavity, reduced-pressure treatment device 102, 302, 402) or system will now be presented. The system is particularly suitable for temporary bridging of abdominal wall openings where primary closure may not be readily possible and or repeat abdominal entries are necessary. The illustrative system described here may be used with open abdominal wounds, with exposed viscera, including but not limited to abdominal compartment syndrome. Before applying the system, typically hemostasis should be achieved.

In deploying the open-cavity, reduced-pressure treatment system, the reduced-pressure treatment device preferably covers all exposed viscera and preferably separates completely the viscera from contact with the abdominal wall. For example, the lower surface of the reduced pressure treatment device, such as drape 148, can be sized and shaped to permit coverage. The reduced-pressure treatment device may be placed over the omentum or exposed internal organs, and carefully tucked between the abdominal wall and internal organs. In doing so, the healthcare provider may use the reduced-pressure treatment device to completely separate the abdominal wall from the internal organs.

To prepare for deployment of the system, any sharp edges or bone fragments are eliminated from wound area or covered. The abdominal wound is irrigated and the periwound area cleaned. The periwound tissue at the epidermis is typically dried before further application.

The reduced-pressure treatment device is then sized by determining the appropriate size and cutting. The reduced-pressure treatment device is initially unfolded in a sterile field. Either side of the reduced-pressure treatment device may be placed on the omentum or viscera. The reduced-pressure treatment device is gently placed over the open abdominal cavity. The orientation of the reduced-pressure treatment device for the specific application is determined. If the reduced-pressure treatment device will be placed around tubes, drains or the falciform ligament, the reduced-pressure device is cut only between the plurality of encapsulated leg members. The reduced-pressure treatment device is placed in the proper orientation before cutting.

The reduced-pressure treatment device is then folded to size and used that way or may be cut. The healthcare provider holds the reduced-pressure treatment device by the edge and slightly lifts the reduced-pressure treatment device. The reduced-pressure treatment device is slowly lowered into the paracolic gutter with one hand and the other hand is used to gently and evenly work the reduced-pressure treatment device down. The healthcare provider folds any excess portions of the reduced-pressure treatment device up and over onto itself. The healthcare provider continues to place the reduced-pressure treatment device between abdominal wall and internal organs throughout the abdominal compartment. The healthcare provider preferably provides full coverage of all viscera. The reduced-pressure treatment device may then be cut as needed for sizing outside of the wound.

To size the device, the reduced-pressure treatment device can be cut through center of one of the large manifold squares, or leg modules, using sterile scissors. In this illustrative embodiment, the cut is not made through the manipulation zone, but through the leg module. The healthcare provider then pinches the remaining half of the foam square, or leg module, and the adjacent, inboard manipulation zone through the encapsulating member with one hand and pulls the manifold material. The manifold material in the leg module and the manipulation zone will separate at the next square, or leg module. This will ensure that edges of the reduced-pressure treatment device cover the otherwise exposed manifold edge. The manifold material, e.g., foam, preferably does not contact organs.

The manifold that is to be placed on top of the central connection member is next prepared. In this embodiment, the manifold may be a perforated foam manifold that has perforations to help tear the manifold to the desired size. The manifold preferably fits directly over the reduced-pressure treatment device while still being in contact with wound edges. The manifold should not contact intact skin. Two or more manifolds may be used in some instances. Then, the sized manifold is gently placed into the wound cavity over the reduced-pressure treatment device. The healthcare provider preferably takes care to avoid the manifold going below the level of the abdominal incision or wound.

A drape, or over-drape, is then applied. To apply the drape, a backing is removed from an adhesive layer on one side of the drape and the drape is applied. The drape covers the manifold and a portion of intact epidermis. Preferably the drape covers at least an 8-10 centimeter border of intact periwound tissue. Additional drape material may be added to seal any difficult areas.

The reduced-pressure interface, or interface pad, is then added. The healthcare provider chooses an application site. The site is chosen to optimize fluid flow as well as to facilitate easy tubing positioning. The healthcare provider pinches the drape and cuts a 2.5 cm hole (preferably not a slit) through the drape. The interface pad, which has a central disc and a surrounding outer adhesive skirt, is applied. The interface pad is applied by removing backing layers on an inward-facing surface of the interface pad to expose an adhesive. The interface pad opening in the central disc is placed directly over the hole in the drape. Pressure is gently applied on the central disc and the outer skirt to ensure complete adhesion of the interface pad. One or more stabilization layers may then be removed from a first side of the skirt. The system is now ready for the application of reduced pressure.

Figure 5:
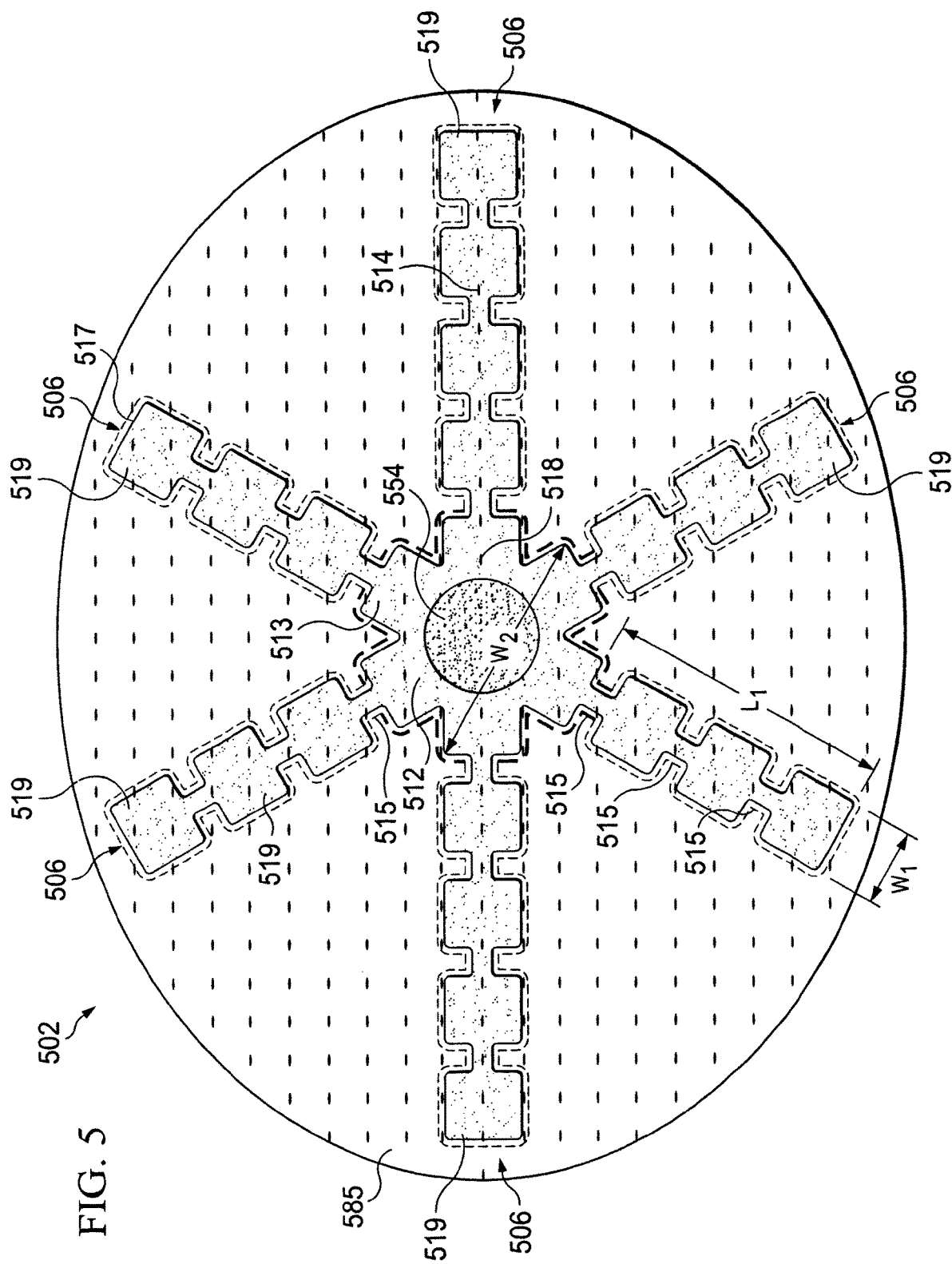
FIG. 5 is a schematic, plan view of another illustrative embodiment of an open-cavity, reduced-pressure treatment device.

According to another illustrative embodiment, which is shown in FIG. 5, an open-cavity, reduced-pressure treatment device 502 includes a central fluid hub 512 and a plurality of elongate members 506. The central fluid hub 512 has an upper surface 513 and a lower surface. The central fluid hub 512 includes a foam manifold 554, which defines at least a portion of the upper surface 513, and a substantially fluid impermeable wall, which defines at least a portion of the lower surface. The fluid impermeable wall includes a plurality of apertures 518. The plurality of elongate members 506 have a proximal end 515, distal end 517, and upper 519 and lower surfaces. The elongate members 506 include a foam enclosed within substantially fluid impermeable walls. The proximal ends 515 of the plurality of elongate members 506 are in fluid communication with the central fluid hub 512. The elongate members 506 include apertures 514 extending through the fluid impermeable wall along at least a portion of the lower surface of the elongate members 506.

The plurality of elongate members 506 have a first length L1 extending from the central fluid hub 512 and a first width ($W_1$) generally parallel to the upper surface and perpendicular to the first length. The central hub has a second width ($W_2$) between lateral edges on a portion between a first and second elongate member. The second width is greater than the first width ($W_2 > W_1$). The plurality of elongate members 506 are fluidly coupled to the central hub 512. The open-cavity, reduced-pressure treatment device 502 may have an aspect ratio of the plurality of elongate members 506 in the range of 3.0 to 10.0. The open-cavity, reduced-pressure treatment device 502 may have an aspect ratio of the plurality of elongate members 506 that is greater than 3.5. The open-cavity, reduced-pressure treatment device 502 may also include an elastic material 585 extending between the plurality of elongate members 506.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in a connection to any one embodiment may also be applicable to any other embodiment.

We claim:

1. A treatment device, comprising:
  a central fluid hub having an upper surface and a lower surface, the fluid hub including a foam manifold defining at least a portion of the upper surface and a substantially fluid impermeable wall defining at least a portion of the lower surface, the fluid impermeable wall including a plurality of apertures; and
  a plurality of elongate members having a proximal end, a distal end, an upper surface, and a lower surface, the elongate members including a foam enclosed within a substantially fluid impermeable wall material, the proximal ends of the plurality of elongate members in fluid communication with the central fluid hub, the elongate members including apertures extending through the substantially fluid impermeable wall material along at least a portion of the lower surface of the elongate members.

2. The treatment device of claim 1, wherein:
the plurality of elongate members have a length extending from the central fluid hub and a first width generally parallel to the upper surface;
the central fluid hub has a second width between a first elongate member and a second elongate member;
the second width is greater than the first width; and
an aspect ratio of the plurality of elongate members is in the range of 3.0 to 10.0.

3. The treatment device of claim 1, wherein:
the plurality of elongate members have a length extending from the central fluid hub and a first width generally parallel to the upper surface;
the central fluid hub has a second width between a first elongate member and a second elongate member;
the second width is greater than the first width; and
an aspect ratio of the plurality of elongate members is greater than 3.5.

4. The treatment device of claim 1, further comprising a substantially fluid impermeable material extending between the plurality of elongate members.

5. The treatment device of claim 1, further comprising an expandable material extending between the plurality of elongate members.

6. The treatment device of claim 1, wherein the central fluid hub and the plurality of elongate fluid members are configured to be disposed adjacent to a tissue site.

7. The treatment device of claim 1, wherein the lower surface of the plurality of elongate members is configured to substantially contact a tissue site along a length of the elongate member.

8. A treatment device, comprising:
a fluid hub including an upper surface, a lower surface, a foam manifold, and a substantially fluid impermeable wall defining at least a portion of the lower surface, the fluid impermeable wall including a plurality of apertures; and
a plurality of elongate members including an upper surface, a lower surface, and a foam enclosed within a substantially fluid impermeable wall material, the plurality of elongate members in fluid communication with the fluid hub and including apertures extending through the substantially fluid impermeable wall material along at least a portion of the lower surface of the elongate members;
wherein the lower surface of the plurality of elongate members is configured to substantially contact a tissue site along a length of the elongate member.

9. The treatment device of claim 8, wherein:
the plurality of elongate members have a length extending from the fluid hub and a first width generally parallel to the upper surface;
the fluid hub has a second width between a first elongate member and a second elongate member;
the second width is greater than the first width; and
an aspect ratio of the plurality of elongate members is in the range of 3.0 to 10.0.

10. The treatment device of claim 8, wherein:
the plurality of elongate members have a length extending from the fluid hub and a first width generally parallel to the upper surface;
the fluid hub has a second width between a first elongate member and a second elongate member;
the second width is greater than the first width; and
an aspect ratio of the plurality of elongate members is greater than 3.5.

11. The treatment device of claim 8, further comprising a substantially fluid impermeable material extending between the plurality of elongate members.

12. The treatment device of claim 8, further comprising an expandable material extending between the plurality of elongate members.

13. The treatment device of claim 8, wherein the fluid hub and the plurality of elongate fluid members are configured to be disposed adjacent to a tissue site.

14. The treatment device of claim 8, wherein the foam manifold defines at least a portion of the upper surface of the fluid hub.

* * * * *